US007621269B2

(12) United States Patent
Turiello

(10) Patent No.: US 7,621,269 B2
(45) Date of Patent: *Nov. 24, 2009

(54) BREATHABLE AIR SAFETY SYSTEM AND METHOD HAVING AT LEAST ONE FILL SITE

(75) Inventor: Anthony J. Turiello, Redwood City, CA (US)

(73) Assignee: Rescue Air Systems, Inc., San Carlos, CA (US)

( * ) Notice: Subject to any disclaimer, the term of this patent is extended or adjusted under 35 U.S.C. 154(b) by 351 days.

This patent is subject to a terminal disclaimer.

(21) Appl. No.: 11/505,708

(22) Filed: Aug. 16, 2006

(65) Prior Publication Data

US 2008/0041379 A1 Feb. 21, 2008

(51) Int. Cl.
*A61M 16/00* (2006.01)
*A62B 9/00* (2006.01)

(52) U.S. Cl. ............................ 128/204.21; 128/200.24; 128/204.18; 128/204.26; 128/206.22

(58) Field of Classification Search ............ 128/200.24, 128/201.24, 203.27, 204.18, 204.21, 205.26, 128/897, 898; 52/2.1, 169.6, 302.1, 173.3; 454/169–172
See application file for complete search history.

(56) References Cited

U.S. PATENT DOCUMENTS

| | | | | | |
|---|---|---|---|---|---|
| 281,027 | A | * | 7/1883 | Cottier | 454/368 |
| 465,298 | A | * | 12/1891 | Timby | 165/48.1 |
| 472,163 | A | * | 4/1892 | Duffy | 454/252 |
| 835,075 | A | * | 11/1906 | Mahappy | 128/207.12 |
| 1,005,196 | A | * | 10/1911 | Gold et al. | 454/172 |
| 1,413,275 | A | * | 4/1922 | Howard | 116/214 |
| 2,014,840 | A | * | 9/1935 | Geiger et al. | 454/252 |
| 2,299,793 | A | * | 10/1942 | Cleve et al. | 128/202.13 |
| 2,855,926 | A | * | 10/1958 | Koppelman | 128/202.13 |
| 3,739,707 | A | * | 6/1973 | Knapp | 454/228 |
| 3,945,800 | A | * | 3/1976 | Roos | 431/345 |
| 3,973,562 | A | * | 8/1976 | Jansson | 128/205.12 |
| 3,995,626 | A | * | 12/1976 | Pearce, Jr. | 128/205.24 |
| 4,058,253 | A | * | 11/1977 | Munk et al. | 236/46 R |
| 4,153,083 | A | * | 5/1979 | Imler et al. | 141/4 |
| 4,165,738 | A | * | 8/1979 | Graves et al. | 128/202.13 |
| 4,331,139 | A | * | 5/1982 | Popa | 128/202.13 |

(Continued)

OTHER PUBLICATIONS

"New Firefighter Air System Makes High-Rise Fire-Fighting Safer; APS Stairwell Air-Replenishment System First of Its Kind in Arizona". Business Wire. Apr. 27, 2004.*

*Primary Examiner*—Justine R Yu
*Assistant Examiner*—Annette F Dixon
(74) *Attorney, Agent, or Firm*—Raj Abhyanker, LLP

(57) ABSTRACT

A breathable air safety system and method having at least one fill site is disclosed. In one aspect, a method of safety of a structure is disclosed. A prescribed pressure of an emergency support system is ensured to be within a threshold range of the prescribed pressure by including a valve of the emergency support system to prevent leakage of breathable air from the emergency support system. The prescribed pressure of the emergency support system is designated based on a municipality code that specifies a pressure rating of the breathable air apparatus that is used in an authority agency of a particular geographic location. An air extraction process is expedited from the emergency support system by including a RIC (rapid interventions company/crew) /UAC (universal air connection) fitting to a fill panel to fill a breathable air apparatus.

15 Claims, 15 Drawing Sheets

U.S. PATENT DOCUMENTS 4,353,292 A * 10/1982 Almasi et al. ............... 454/168
4,380,187 A * 4/1983 Wicks ........................ 454/342
4,413,622 A * 11/1983 Austin ................... 128/205.25
4,467,796 A * 8/1984 Beagley ................. 128/202.13
4,510,930 A * 4/1985 Garcia ................... 128/202.22
4,542,774 A * 9/1985 Stavlo ........................... 141/1
4,712,594 A * 12/1987 Schneider ................... 141/114
4,862,931 A * 9/1989 Vella ............................. 141/1
5,131,269 A * 7/1992 Blosnick et al. ............... 73/129
5,570,685 A * 11/1996 Turiello ................. 128/202.13
5,800,260 A * 9/1998 Kao ........................... 454/370
5,809,999 A * 9/1998 Lang ..................... 128/200.24
5,979,440 A * 11/1999 Honkonen et al. ..... 128/201.21
6,474,334 B1 * 11/2002 Lemer ................... 128/204.18
6,701,923 B2 * 3/2004 Cazenave et al. ...... 128/204.22
6,948,498 B2 * 9/2005 Cazenave et al. ...... 128/204.22
7,055,780 B2 * 6/2006 Phillips ................... 244/118.5
7,204,249 B1 * 4/2007 Richey et al. .......... 128/204.18
7,255,104 B2 * 8/2007 Phillips ................. 128/204.22
2006/0219842 A1 * 10/2006 Shell et al. ............... 244/118.5

* cited by examiner

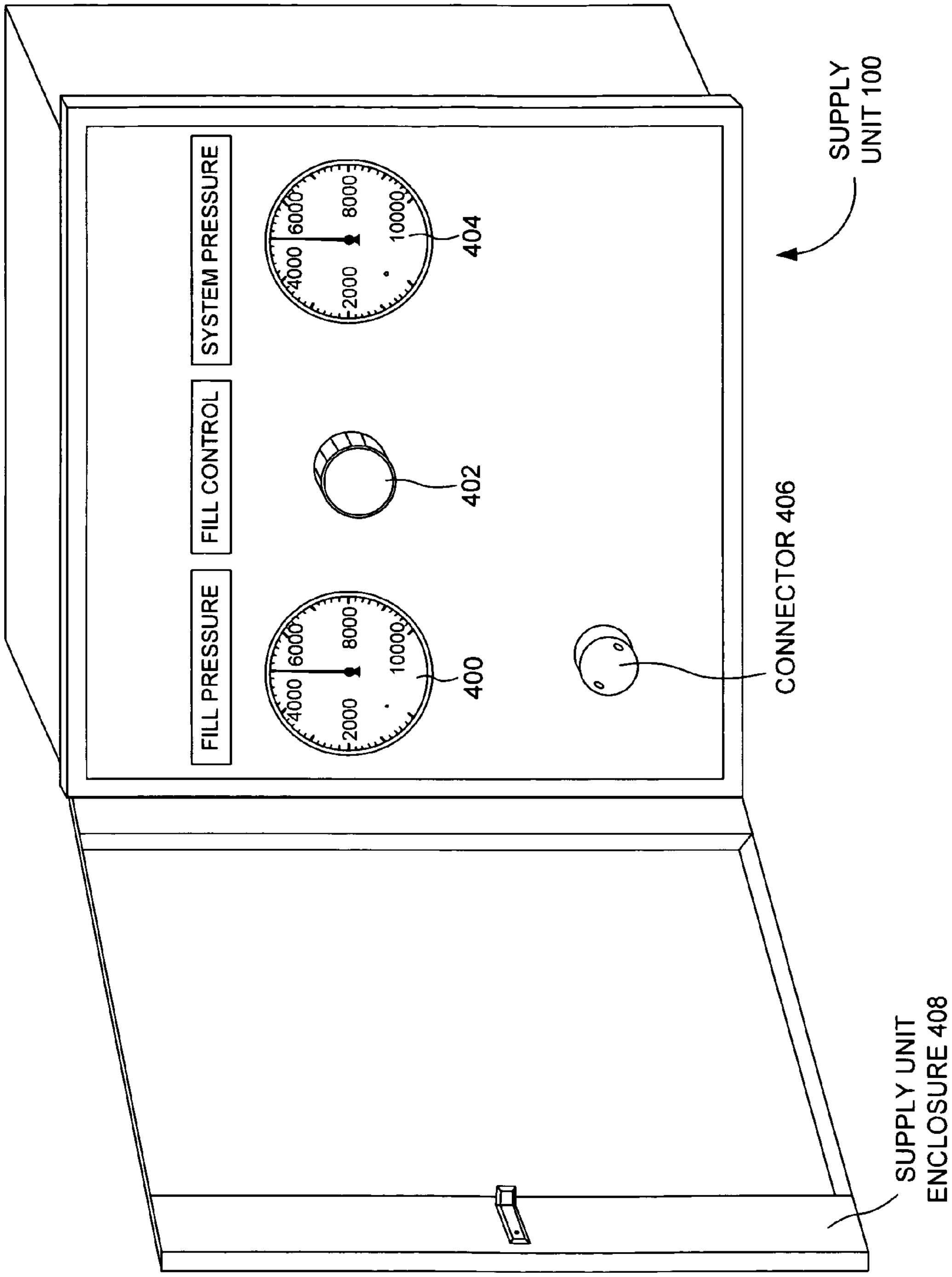
FIGURE 4A (FRONT VIEW)

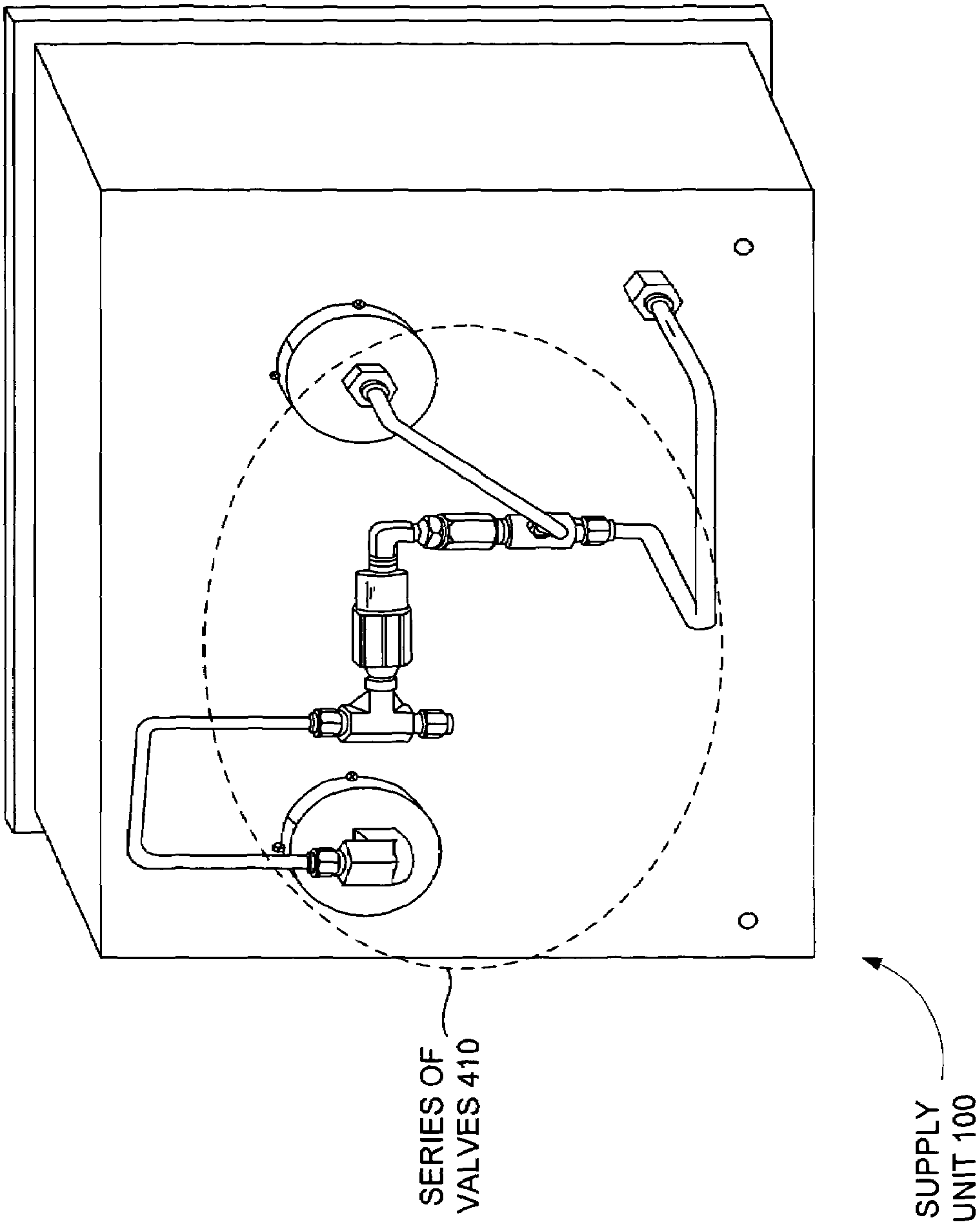
FIGURE 4B (REAR VIEW)

BREATHABLE AIR SAFETY SYSTEM AND METHOD HAVING AT LEAST ONE FILL SITE

FIELD OF TECHNOLOGY

This disclosure relates generally to the technical fields of safety systems and, in one example embodiment, to a safety system and method having at least one fill site.

BACKGROUND

In a case of an emergency situation of a structure (e.g., a horizontal building structure such as a shopping mall, warehouse, storage and manufacturing facilities, large box stores such as IKEA and/or Home Depot, a vertical building structure such as a high rise building, a mid rise building, and/or a low rise building, a mine, a subway, a tunnel and/or a wine cave, etc.), emergency personnel (e.g., a firefighter, a SWAT team, a law enforcer, and/or a medical worker, etc.) may be deployed on-site of the structure to alleviate the emergency situation through mitigating a source of hazard as well as rescuing stranded civilians from the structure. The emergency situation may include events such as a building fire, a chemical attack, terror attack, subway accident, mine collapse, and/or a biological agent attack.

In such situations, breathable air inside the structure may be hazardously affected (e.g., depleted, absorbed, and/or contaminated). In addition, flow of fresh air into the structure may be significantly hindered due to the structure having enclosed regions, lack of windows, and/or high concentration of contaminants. As a result, inhaling air in the structure may be extremely detrimental and may further result in death (e.g., within minutes). Furthermore, emergency work may often need to be performed from within the structure (e.g., due to a limitation of emergency equipment able to be transported on a ground level).

The emergency personnel's ability to alleviate the emergency in an efficient manner may be significantly limited by the lack of breathable air and/or the abundance of contaminated air. Survival rate in the structure may substantially decrease due to a propagation of contaminated air throughout the structure placing a large number of lives at significant risk.

As such, the emergency personnel may utilize a portable breathable air apparatus (e.g., self-contained breathable air apparatus) as a source of breathable air during an emergency incident and/or rescue mission. However, the portable breathable air apparatus may be heavy (e.g., 20-30 pounds) and may only provide breathable air for a short while (e.g., approximately 15-30 minutes). In the emergency situation, the emergency personnel may need to walk, ascend and/or descend to a particular location within the structure to perform rescuing work (e.g., due to inoperable transport systems such as obstructed walkway, elevators, moving sidewalks, and/or escalators, etc.). As such, by the time the emergency personnel reaches the particular location, his/her portable breathable air apparatus may have already depleted and may require replenishment (e.g., via a shuttle method or returning back to the ground floor for a new portable breathable air apparatus). As a result, precious lives may be lost due to precious time being lost.

SUMMARY

A safety system and method having at least one fill site are disclosed. In one aspect, a safety system of a structure includes a supply unit of a building structure to facilitate delivery of breathable air from a source of compressed air to an air distribution system of the building structure, a valve to prevent leakage of the breathable air from the air distribution system potentially leading to loss of system pressure, a fill panel interior to the building structure having a RIC/UAC fitting pressure rated for a fill outlet of the fill panel to fill a breathable air apparatus to expedite a breathable air extraction process from the air distribution system and to provide the breathable air to the breathable air apparatus at multiple locations of the building structure, and a distribution structure that is compatible with use with compressed air that facilitates dissemination of the breathable air of the source of compressed air to multiple locations of the building structure.

The system may include a supply unit enclosure encompassing the supply unit having any of a weather resistant feature, ultraviolet and infrared solar radiation resistant feature to prevent corrosion and physical damage. The system may also include a locking mechanism of the supply unit enclosure and a fill panel enclosure of the fill panel to secure the supply unit and the fill panel from intrusions that potentially compromise safety and reliability of the air distribution system. Further, the system may include at least an 18 gauge carbon steel of the supply unit enclosure that minimizes physical damage due to various hazards by protecting the supply unit from any of an intrusion and damage.

The system may also include a valve of the supply unit to perform any of a suspension of transfer and a reduction of flow of breathable air from the source of compressed air to the air distribution system when useful. The system may include a safety relief valve of any of the supply unit and the fill panel set to have an open pressure of at most approximately 10% more than a design pressure of the air distribution system to ensure reliability of the air distribution system through maintaining the system pressure such that it is within a threshold range of a pressure rating of each component of the air distribution system. Further, any of a CGA connector and a RIC/UAC connector of the supply unit to facilitate a connection with the source of compressed air through ensuring compatibility with a connector of the source of compressed air. The system may include an adjustable pressure regulator of the supply unit to adjust a fill pressure of the source of compressed air to ensure that the fill pressure does not exceed the design pressure of the air distribution system.

In addition, the system may include at least one pressure gauge of the supply unit enclosure to indicate any of the system pressure of the air distribution system and the fill pressure of the source of compressed air and a visible marking of the supply unit enclosure and the fill panel enclosure to provide (high visibility) luminescence in a reduced light environment. The fill panel enclosure may comprise of substantially 18 gauge carbon steel to minimize physical damage of various naturally occurring and man-imposed hazards through protecting the fill panel from any of an intrusion and damage The system may include a valve of the fill panel to prevent leakage of air from the air distribution system potentially leading to pressure loss of the air distribution system through ensuring that the system pressure is maintained within a threshold range of the design pressure to reliably fill the breathable air apparatus. The system may include an isolation valve of the fill panel to isolate a fill panel from a remaining portion of the air distribution system.

Further, the system may include at least one pressure regulator of the fill panel to adjust the fill pressure to fill the breathable air apparatus and to ensure that the fill pressure does not exceed the pressure rating for the RIC/UAC fitting. The system may include at least one pressure gauge of the fill station to indicate any of a fill pressure of the fill panel and a system pressure of the air distribution system. Further, any of a fire rated material and a fire rated assembly may enclose the distribution structure such that the distribution structure has the ability to withstand elevated temperatures for a prescribed period of time. The system may include a robust solid casing of the distribution structure system to prevent physical damage to the distribution structure system potentially compromising the safety and integrity of the air distribution system (emergency support system). Each fill outlet of the fill panel is couple-able to any of a self-contained breathable air apparatus and a respiratory mask having a compatible RIC/UAC connector to deliver the breathable air. The distribution structure may include any of a stainless steel and a thermoplastic material that is compatible for use with compressed air.

In another aspect, a method of a building structure includes ensuring that a prescribed pressure of an emergency support system maintains within a threshold range of the prescribed pressure by including a valve of the emergency support system to prevent leakage of breathable air from the emergency support system, and expediting an air extraction process from the emergency support system by including a RIC/UAC fitting to a fill panel to fill a breathable air apparatus.

The method may also include providing protection against any of fire and physical damage to a distribution structure that couples the supply unit and a fill site to transfer breathable air from the source of compressed air to the fill site, And ensuring that the distribution structure withstands elevated temperatures for a period of time through any of an enclosing the distribution structure in any of the fire rated material and assembly that embeds the distribution structure in a fire rated assembly of the building structure that is fire rated. In addition, the method further includes providing any of a tamper resistant shielding and a corrosion preventive shielding for the distribution structure such that unauthorized access and natural wear to the distribution structure is prevented through an enclosure of the distribution structure in a robust material. A tamper resistant shielding and a corrosion preventive shielding may be provided for the distribution structure system such that unauthorized access and natural wear to the distribution structure system is prevented through an enclosure of the distribution structure system in a robust material.

Intrusion of the supply unit and the fill panel potentially compromising the safety and reliability of the breathing emergency support system may be prevented by incorporating a locking mechanism of the Supply unit enclosure and a fill panel enclosure. Further, physical damage of various external hazards may be minimized to protect the supply unit and the fill panel from any of an intrusion and damage through utilizing a robust carbon steel to the Supply unit enclosure. Transfer of breathable air may be suspended from the source of compressed air to the emergency support system through utilizing a valve of the supply unit when necessary. The system pressure may be automatically adjusted when it exceeds the prescribed pressure of the emergency support system by a prescribed amount through automatically triggering a safety valve of any of an Supply unit and or a fill panel.

In addition, a fill pressure may of the supply unit may be adjusted to ensure that the fill pressure of the source of compressed air does not exceed the prescribed pressure of the emergency support system to maintain reliability of the emergency support system through adjusting a pressure regulator of the supply unit. The system pressure of the emergency support system and the fill pressure of the source of compressed air may be automatically monitored through the pressure gauge of the supply unit enclosure. Accessibility of the supply unit enclosure and the fill panel enclosure may be improved through providing luminescence in reduced light environments (emergency incident situations) by incorporating a visible marking. Physical damage of various external hazards may be minimized to protect the fill panel and the supply unit from any of an intrusion and damage through utilizing at least substantially an 18 gauge carbon steel of the fill panel enclosure and the supply unit enclosure. Leakage of air from the emergency support system potentially leading to pressure loss of the emergency support system may be prevented through utilizing a valve of the fill panel.

A fill panel may be isolated from a remaining portion of the emergency support system by incorporating an isolation valve to the fill panel such that the remaining portion of the emergency support system is utilizable in an emergency situation.

A fill pressure of the fill panel may be adjusted to ensure that the fill pressure of the fill panel does not exceed the pressure rating for the RIC/UAC fitting.

The prescribed pressure of the emergency support system may be designated base on a municipality code that specifies a pressure rating of the breathable air apparatus that is used in an authority agency of a particular geographical location.

In yet another aspect, a structure may include a first set of walls extending vertically and horizontally enclosing an area of land such that the area of land is in the internal region of the building structure, a second set of walls that divide the internal region of the building structure in any of a horizontal and vertical direction into areas displaced any of a horizontally and vertically from one another, a supply unit adjacent to a particular wall of the first set of walls to facilitate delivery of breathable air from a source of compressed air to an emergency support system of the building structure, a fill panel of the internal region of the building structure having a RIC/UAC fitting to expedite a breathable air extraction process from the emergency support system and to provide the breathable air to the breathable air apparatus at multiple locations of the building structure, and a distribution structure that is compatible with use with compressed air that facilitates dissemination of the breathable air of the source of compressed air to multiple locations of the building structure.

The building structure may also include an air monitoring system to automatically track and record any impurities and contaminants in the breathable air of the air distribution system, an air pressure monitor that is electrically coupled to an alarm such that the alarm is set off when the system pressure of the air distribution system is outside a prescribed threshold range, and a physical enclosure of the fill station exterior to the secure chamber of the fill station that provides additional protection to the fill station from any of an elevated temperature or physical impact.

The methods, systems, and apparatuses disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which:

FIG. 4A is a front view of a supply unit, according to one embodiment.

FIG. 4B is a rear view of a supply unit, according to one embodiment.

Figure 1:
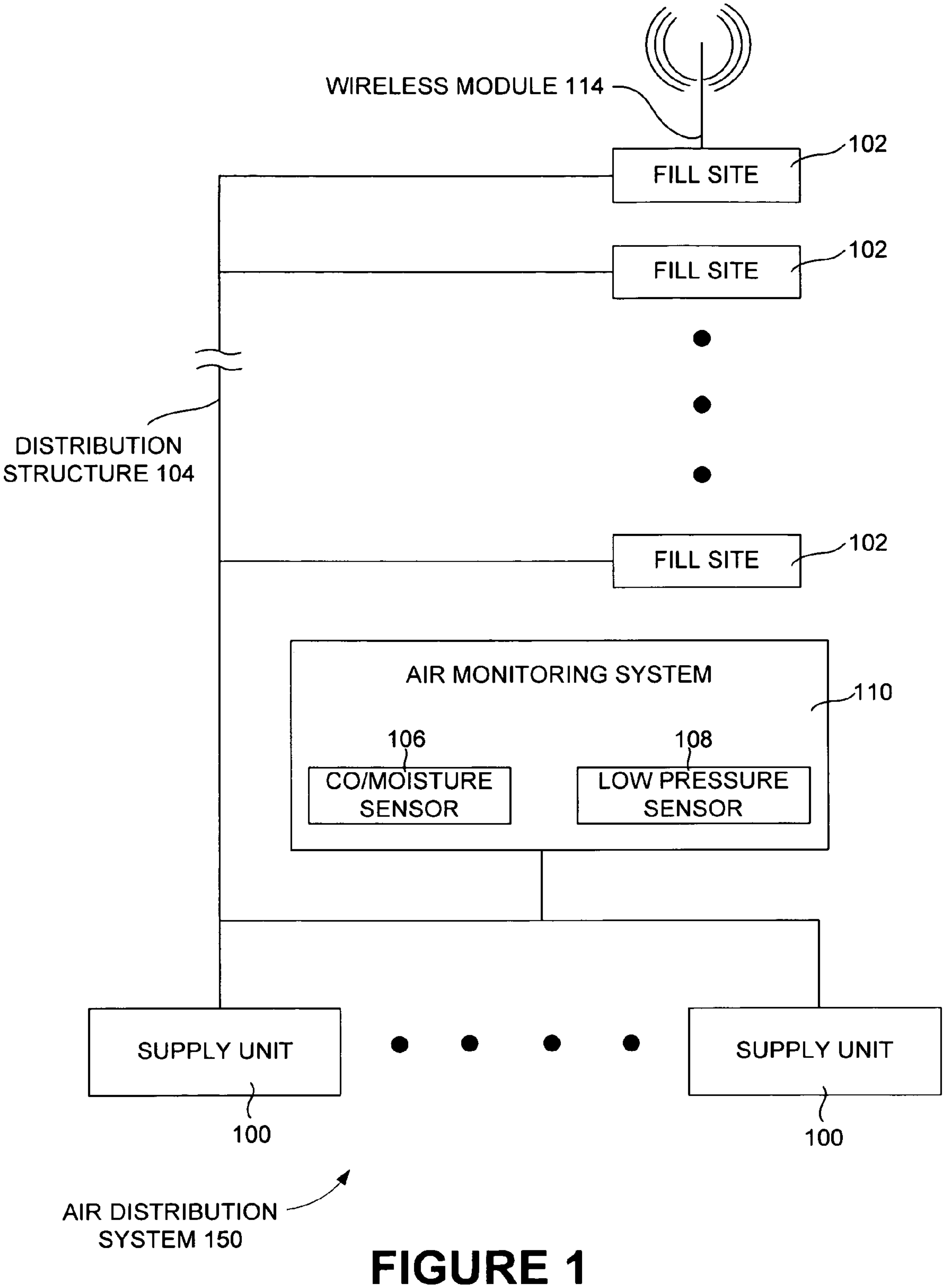
FIG. 1 is a diagram of an air distribution system in a building structure, according to one embodiment.

Other features of the present embodiments will be apparent from the accompanying drawings and from the detailed description that follows.

DETAILED DESCRIPTION

A safety system and method having at least one fill panel are disclosed. In the following description, for the purposes of explanation, numerous specific details are set forth in order to provide a thorough understanding of the various embodiments. It will be evident, however to one skilled in the art that the various embodiments may be practiced without these specific details.

In one embodiment, a safety system of a building structure includes a supply unit (e.g., a supply unit 100 of FIGS. 1-3) of a building structure to facilitate delivery of breathable air from a source of compressed air to an air distribution system (e.g., an air distribution system 150,250,350 of FIGS. 1-3) of the building structure, a valve to prevent leakage of the breathable air from the air distribution system potentially leading to loss of system pressure, a fill site (e.g., a fill site 102A of FIG. 6) interior to the building structure having a RIC (rapid interventions company/crew)/UAC (universal air connection) fitting pressure rated for a fill outlet of the fill panel to fill a breathable air apparatus to expedite a breathable air extraction process from the air distribution system and to provide the breathable air to the breathable air apparatus at multiple locations of the building structure, and a distribution structure (e.g., a distribution structure 104 of FIGS. 1-3) that is compatible with use with compressed air that facilitates dissemination of the breathable air of the source of compressed air to multiple locations of the building structure.

In another embodiment, a method may include ensuring that a prescribed pressure of the emergency support system (e.g., the air distribution system 150,250,350 of FIGS. 1-3) maintains within a threshold range of the prescribed pressure by including a valve of the emergency support system to prevent leakage of breathable air from the emergency support system, and expediting an air extraction process from the emergency support system by including a RIC (rapid interventions company/crew)/UAC (universal air connection) fitting to a fill panel to fill a breathable air apparatus.

In yet another embodiment, a building structure may include a first set of walls extending vertically and horizontally enclosing an area of land such that the area of land is in the internal region of the building structure, a second set of walls that divide the internal region of the building structure in any of a horizontal and vertical direction into areas displaced any of a horizontally and vertically from one another, a supply unit (e.g., the supply unit 100 of FIGS. 1-3) adjacent to a particular wall of the first set of walls to facilitate delivery of breathable air from a source of compressed air to an emergency support system (e.g., the air distribution system 150, 250,350 of FIGS. 1-3) of the building structure, a fill panel of the internal region of the building structure having a RIC (rapid interventions company/crew)/UAC universal air connection fitting to expedite a breathable air extraction process from the emergency support system and to provide the breathable air to the breathable air apparatus at multiple locations of the building structure, and or a distribution structure (e.g., a distribution structure 104 of FIGS. 1-3) that is compatible with use with compressed air that facilitates dissemination of the breathable air of the source of compressed air to multiple locations of the building structure.

FIG. 1 is a diagram of an air distribution system 150 in a building structure, according to one embodiment. The air distribution system 150 may include any number of supply unit 100, any number of fill site 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. The supply unit 100 may be placed at a number of locations exterior to the building structure (e.g., a horizontal building structure such as a shopping mall, IKEA, Home Depot, a vertical building structure such as a high rise building, a mid rise building, and/or a low rise building, a mine, a subway, and/or a tunnel, etc.) to allow ease of access by a source of compressed air and/or to expedite supplying the air distribution system 150 with breathable air. The supply unit 100 may also be placed at locations that are substantially free of traffic (e.g., parked cars, vehicle movement, and/or human traffic, etc.) to decrease potential obstruction that may be present in an emergency situation (e.g., a building fire, a chemical attack, terror attack, subway accident, mine collapse, and/or a biological agent attack, etc.).

The fill site 102 may also be placed at a number of locations of the building structure (e.g., a horizontal building structure such as a shopping mall, IKEA, Home Depot, a vertical building structure such as a high rise building, a mid rise building, and/or a low rise building, a mine, a subway, and/or a tunnel, etc.) to provide multiple access points to breathable air in the building structure. The building structure may have any number of fill site 102 (e.g., a fill panel and/or a fill station, etc.) on each floor and/or have any number of fill site 102 (e.g., a fill panel and/or a fill station, etc.) on different floors. Each fill site 102 may be sequentially coupled to one another and to the supply unit 100 through the distribution structure 104. The distribution structure 104 may include any number of pipes to expand an air carrying capacity of the air distribution system 150 such that breathable air may be replenished at a higher rate. In addition, the fill site 102 may include wireless capabilities (e.g., a wireless module 114) for communication with remote entities (e.g., the supply unit 100, building administration, and/or an authority agency, etc.).

The air monitoring system 110 may contain multiple sensors such as the CO/moisture sensor 106 and the pressure sensor 108 to track air quality of the breathable air in the air distribution system 150. Since emergency personnel (e.g., a fire fighter, a SWAT team, a law enforcer, and/or a medical worker, etc.) depend on the breathable air distributed via the air distribution system 150, it is crucial that air quality of the breathable air be constantly maintained. The air monitoring system 110 may also include other sensors that detect other hazardous substances (e.g., benzene, acetamide, acrylic acid, asbestos, mercury, phosphorous, propylene oxide, etc.) that may contaminate the breathable air.

In one embodiment, the distribution structure 104 may be compatible with use with compressed air facilitates dissemination of the breathable air of the source of compressed air to multiple locations of the building structure. A fire rated material may encase the distribution structure 104 such that the distribution structure has the ability to withstand elevated temperatures for a period of time. The pipes of the distribution structure 104 may include a sleeve exterior to the fire rated material to further protect the fire rated material from any damage. Both ends of the sleeve may be fitted with a fire rated material that is approved by an authority agency. In addition, the distribution structure 104 may include a robust solid casing to prevent physical damage to the distribution structure potentially compromising the safety and integrity of the air distribution system.

The distribution structure 104 may include support structures at intervals no larger than five feet to provide adequate structural support for each pipe of the distribution structure 104. The pipes and the fittings of the distribution structure 104 may include any of a stainless steel and a thermoplastic material that is compatible for use with compressed air.

In another embodiment, the air distribution system may include an air monitoring system (e.g., the air monitoring system 110) to automatically track and record any impurities and contaminants in the breathable air of the air distribution system. The air monitoring system (e.g., the air monitoring system 110) may have an automatic shut down feature to suspend air distribution to the fill site 102 in a case that any of an impurity and contaminant concentration exceeds a safety threshold. For example, a pressure monitoring system (e.g., the pressure sensor 108) may automatically track and record the system pressure of the air distribution system. Further, a pressure switch may be electrically coupled to a alarm system such that the fire alarm system is set off when the system pressure of the air distribution system is outside a safety range.

Figure 2:
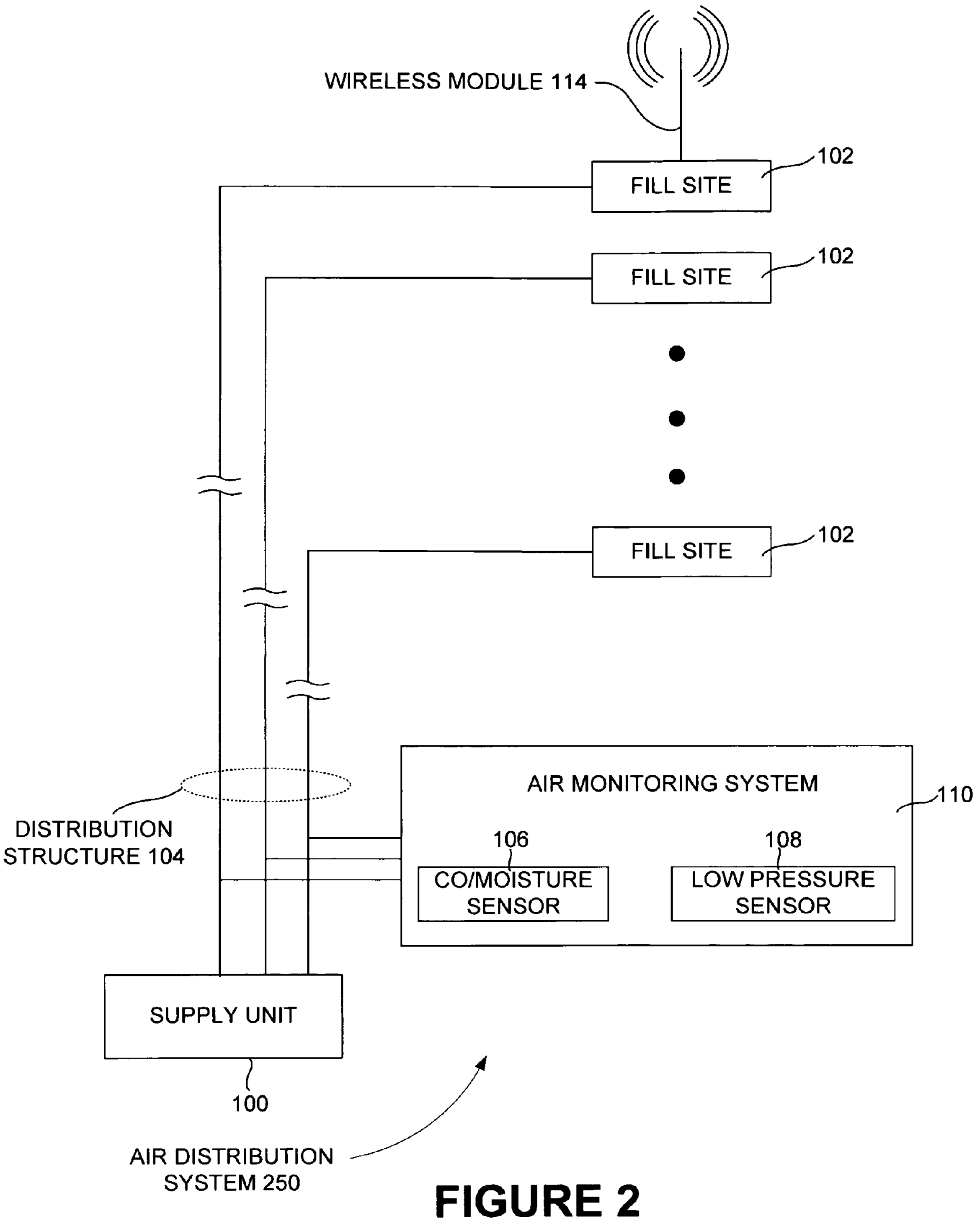
FIG. 2 is another diagram of an air distribution system in a building structure, according to one embodiment.

FIG. 2 is another diagram of an air distribution system 250 in a building structure, according to one embodiment. The air distribution system 250 may include any number of supply unit 100, any number of fill site 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may individually couple each fill site 102 (e.g., a fill panel and/or a fill station, etc.) to a supply unit 100. Individual coupling may be advantageous in that in the case one pipe of the distribution structure 104 becomes inoperable the other pipes can still deliver air to the fill site 102 (e.g., a fill panel and/or a fill station, etc.). The other system components (e.g., the fill site 102, the supply unit 100, and the air monitoring system 110 were described in detail in the previous section).

Figure 3:
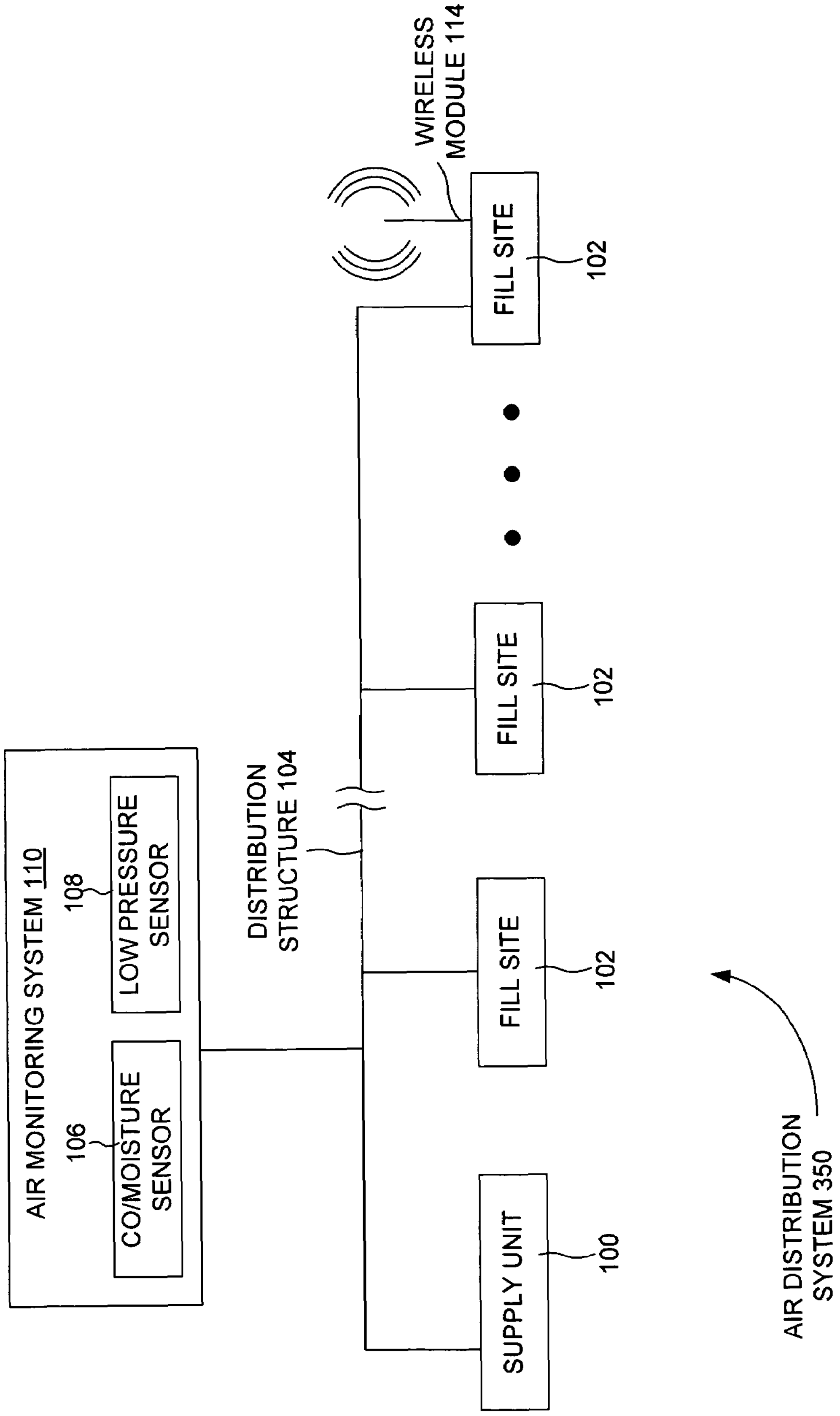
FIG. 3 is a diagram of an air distribution system in a building structure having fill sites located horizontally from one another, according to one embodiment.

FIG. 3 is a diagram of an air distribution system 350 in a building structure having any number of fill site 102 (e.g., a fill panel and/or a fill station, etc.) located horizontally from one another, according to one embodiment.

The air distribution system 350 may include any number of supply unit 100, any number of fill site 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may sequentially couple each fill site 102 (e.g., a fill panel and/or a fill station, etc.) displaced predominantly horizontally from a supply unit 100. Each air distribution system (e.g., the air distribution system 150, 250, 350) may be used in conjunction with one another depending on the particular architectural style of the building structure in a manner that provides most efficient access to the breathable air of the air distribution system reliably. The other system components (e.g., the fill site 102, the supply unit 100, and the air monitoring system 110 were described in detail in the previous section).

FIG. 4A is a front view of a supply unit 100, according to one embodiment.

The supply unit 100 provides accessibility of a source of compressed air to supply air to an air distribution system (e.g., an air distribution system 150, 250, and/or 350). The supply unit may include a fill pressure indicator 400, a fill control knob 402, a system pressure indicator 404, and/or a connector 406. The fill pressure indicator 400 may indicate the pressure level at which breathable air is being delivered by the source of compressed air to the air distribution system (e.g., an air distribution system 150, 250, and/or 350 of FIGS. 1-3). The system pressure indicator 404 may indicate the current pressure level of the breathable air in the air distribution system. The fill control knob 402 may be used to control the fill pressure such that the fill pressure does not exceed a safety threshold that the air distribution system is designed for. The connector 406 may be a CGA connector that is compatible with an air outlet of the source of compressed air of various emergency agencies (e.g., fire station, law enforcement agency, medical provider, and/or SWAT team, etc.). The connector 406 of the supply unit 100 may facilitate a connection with the source of compressed air through ensuring compatibility of the supply unit 100 with the source of compressed air.

The supply unit 100 may include an adjustable pressure regulator of the supply unit 100 that is used to adjust a fill pressure of the source of compressed air to ensure that the fill pressure does not exceed the design pressure of the air distribution system. Further, the supply unit may also include at least one pressure gauge of the supply unit enclosure to indicate any of the system pressure (e.g., the system pressure indicator 404) of the air distribution system and the fill pressure (e.g., the fill pressure indicator 400) of the source of compressed air.

FIG. 4B is a rear view of a supply unit 100, according to one embodiment.

The supply unit also includes a series of valves 410 (e.g., a valve, an isolation valve, and/or a safety relief valve, etc.) to further ensure that system pressure is maintained within a safety threshold of the design pressure of the air distribution system.

The supply unit 100 of a building structure may facilitate delivery of breathable air from a source of compressed air to an air distribution system of the building structure. The supply unit 100 includes the series of valves 410 (e.g., the valve, and/or the safety relief valve, etc.) to prevent a leakage of the breathable air from the air distribution system potentially leading to loss of a system pressure. For example, the supply unit 100 may include the valve of the series of valves 410 to automatically suspend transfer of breathable air from the source of compressed air to the air distribution system when useful. The safety relief valve of the supply unit 100 and/or the fill site 102 may release breathable air when a system pressure of the air distribution system exceeds a threshold value beyond the design pressure to ensure reliability of the air distribution system through maintaining the system pressure such that it is within a pressure rating of each component of the air distribution system.

Figure 5:
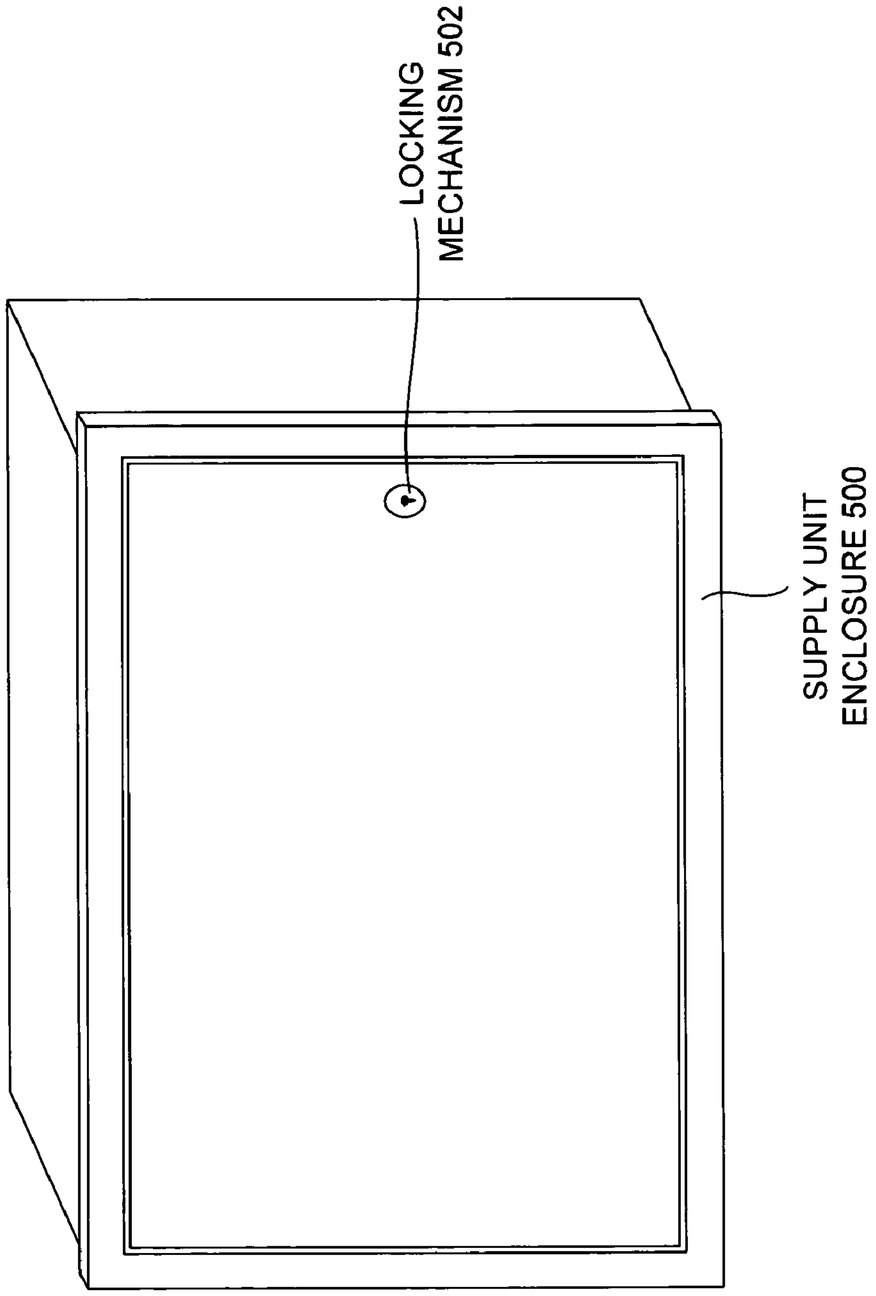
FIG. 5 is an illustration of a supply unit enclosure, according to one embodiment.

FIG. 5 is an illustration of a supply unit enclosure 500, according to one embodiment.

The supply unit enclosure 500 may include a locking mechanism 502 to secure the supply unit 100 from unauthorized access. Further, the supply unit enclosure 500 may also contain fire rated material such that the supply unit 100 is able to withstand burning elevated temperatures.

The supply unit enclosure 500 encompassing the supply unit 100 may have any of a weather resistant feature, ultraviolet and infrared solar radiation resistant feature to prevent corrosion and physical damage. The locking mechanism 502 may secure the supply unit from intrusions that potentially compromise safety and reliability of the air distribution system. In addition, the supply unit enclosure 500 may include a robust metallic material of the supply unit enclosure 500 to minimize a physical damage due to various hazards to protect the supply unit 100 from any of an intrusion and damage. The robust metallic material may be at least substantially 18 gauge carbon steel. The supply unit enclosure 500 may include a visible marking to provide luminescence in a reduced light environment. The locking mechanism 502 may also include a tamper switch such that a alarm is automatically triggered and a signal is electrically coupled to any of a relevant administrative personnel of the building structure and the emergency supervising station when an intrusion of any of the supply unit and the secure chamber occurs.

Figure 6:
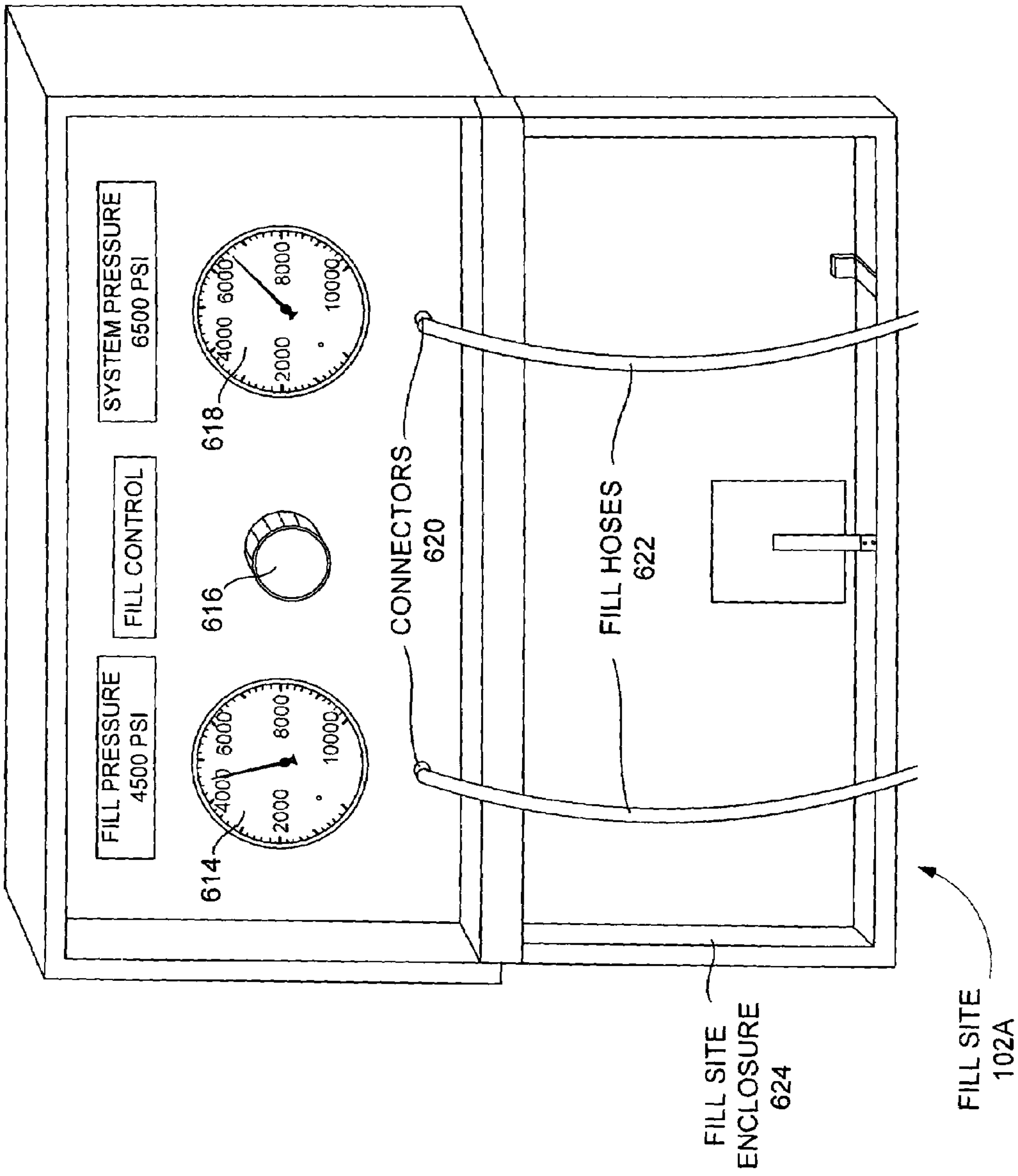
FIG. 6 is an illustration of a fill panel, according to one embodiment.

FIG. 6 is an illustration of a fill site 102A, according to one embodiment.

The fill site 102A (e.g., a fill panel) includes a fill pressure indicator 614 (e.g., pressure gauge), a fill control knob 616 (e.g., pressure regulator), a system pressure indicator 618, a number of connector 620 (e.g., RIC (rapid interventions company/crew)/UAC universal air connection)connector), and or fill hoses 622. The fill site 102A may also include a locking mechanism of a fill site enclosure 624 (e.g., fill panel enclosure) to secure the fill site 102A from intrusions that potentially compromise safety and reliability of the air distribution system. The system pressure indicator 618 may indicate the current pressure level of the breathable air in the air distribution system. The fill control knob 616 (e.g., pressure regulator) may be used to adjust the fill pressure such that the fill pressure does not exceed a safety threshold that the air distribution system is designed for.

The connector 620 may facilitate direct coupling to emergency equipment to supply breathable air through a hose that is connected to the connector 620. In essence, precious time may be saved because the emergency personnel may not need to spend the time to remove the emergency equipment from their rescue attire before they can be supplied with breathable air. Further, the connector 620 connected with the fill hoses 622 may also directly couple to a face-piece of a respirator to supply breathable air to either emergency personnel (e.g., a fire fighter, a SWAT team, a law enforcer, and or a medical worker, etc.) and or stranded survivors in need of breathing assistance. Each of the fill hoses 622 may have different pressure rating of the fill site 102A is couple-able to any of a self-contained breathable air apparatus and respiratory mask having a compatible connector (e.g., RIC (rapid interventions company/crew) /UAC (universal air connection)connector). The fill site enclosure 624 may include a visible marking to provide luminescence in a reduced light environment.

The fill site 102A interior to the building structure may have the connector (e.g., the connector 620) to fill a breathable air apparatus to expedite a breathable air extraction process from the air distribution system and to provide the breathable air to the breathable air apparatus at multiple locations of the building structure. The fill site 102A may include a safety relief valve set to have an open pressure of at most approximately 10% more than a design pressure of the air distribution system to ensure reliability of the air distribution system through maintaining the system pressure such that it is within a threshold range of a pressure rating of each component of the air distribution system. The fill site enclosure 624 may comprise of at least 18 gauge carbon steel to minimize physical damage of various naturally occurring and man-imposed hazards through protecting the fill site from any of an intrusion and damage. The fill site 102A may include an isolation valve to isolate a damaged fill site from a remaining operable portion of the air distribution system.

In an alternate embodiment, a fill station may be a type of fill site 102 of FIG. 1. The fill station may include a system pressure indicator, a regulator, a fill pressure indicator, another fill pressure indicator, and or fill control knob. The fill station may also include a connector (e.g., a RIC (rapid interventions company/crew)/UAC (universal air connection)connector) and multiple breathable air apparatus holders used to supply air from the air distribution system. The fill pressure indicator may indicate the pressure level at which breathable air is being delivered by the source of compressed air to the air distribution system (e.g., an air distribution system 150, 250 and 350 of FIGS. 1-3). The system pressure indicator may indicate the current pressure level of the breathable air in the air distribution system. The fill control knob may be used to control the fill pressure such that the fill pressure does not exceed a safety threshold that the air distribution system is designed for. The connector may facilitate direct coupling to emergency equipment to supply breathable air through a hose that is connected to the connector. In essence, precious time may be saved because the emergency personnel may not need to spend the time to remove the emergency equipment from their rescue attire before they can be supplied with breathable air. Further, the connector may also directly couple to a face-piece of a respirator to supply breathable air.

The multiple breathable air apparatus holders can hold multiple compressed air cylinders to be filled simultaneously. In addition, the multiple breathable air apparatus holders can be rotated such that additional compressed air cylinders may be loaded while the multiple compressed air cylinders are filled inside the fill station. The fill station may be a rupture containment chamber such that over-pressurized compressed air cylinders are shielded and contained to prevent injuries.

In one embodiment, the fill station interior to the building structure may provide the breathable air to a breathable air apparatus at multiple locations of the building structure. A secure chamber of the fill station may be a safety shield that confines a possible rupture of an over-pressurized breathable air apparatus within the secure chamber. The fill station may include a valve to prevent leakage of air from the air distribution system potentially leading to pressure loss of the air distribution system through ensuring that the system pressure is maintained within a threshold range of the design pressure to reliably fill the breathable air apparatus. An isolation valve may be included to isolate a breathable fill station from a remaining portion of the air distribution system.

The isolation valve may be automatically actuated based on an air pressure sensor of the air distribution system. The fill station may include at least one pressure regulator to adjust a fill pressure to fill the breathable air apparatus and to ensure that the fill pressure does not exceed the pressure rating of the breathable air apparatus potentially resulting in a rupture of the breathable air apparatus. The fill station may include at least one pressure gauge to indicate any of a fill pressure (e.g., the fill pressure indicator) of the fill station and a system pressure (e.g., the system pressure indicator) of the air distribution system. In one embodiment, the fill station may have a physical capacity to enclose at least one breathable air apparatus and may include a connector (e.g., a RIC (rapid interventions company/crew)/UAC (universal air connection)connector) to facilitate a filling of the breathable air apparatus. The fill station may also include a securing mechanism of the secure chamber of the fill station having a locking function is automatically actuated via a coupling mechanism with a flow switch that indicates a status of air flow to the breathable air apparatus that is fillable in the fill station.

Figure 7A:
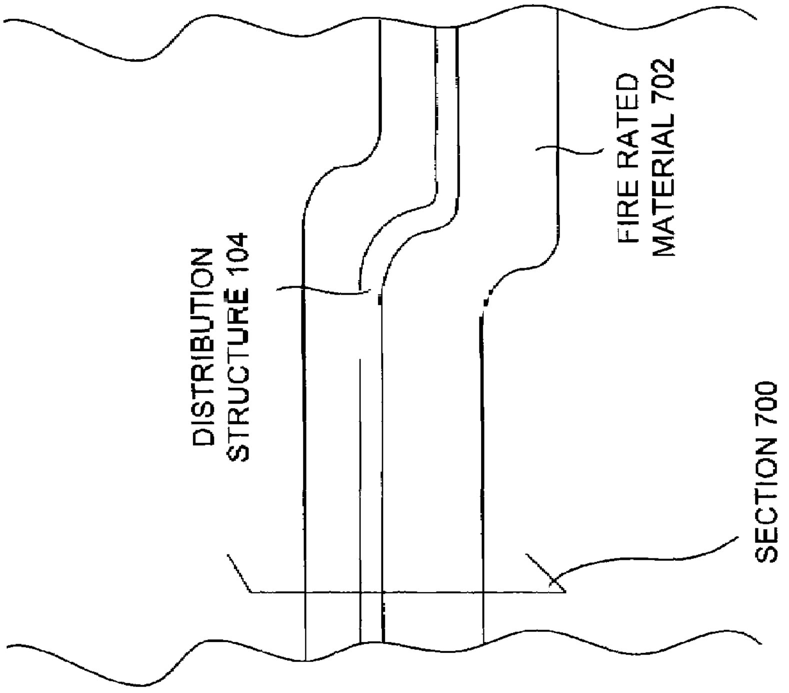
FIG. 7A is a diagrammatic view of a pipe of a distribution structure embedded in a fire rated material, according to one embodiment.

FIG. 7A is a diagrammatic view of a distribution structure 104 embedded in a fire rated material, according to one embodiment.

The distribution structure 104 (e.g., a piping structure) may be enclosed in the fire rated material 702. The fire rated material may prevent the distribution structure 104 from damage in a fire such that an air distribution system (e.g., the air distribution system 150, 250, 350 of FIGS. 1-3) may be operational for a longer time period in an emergency situation (e.g., a building fire, a chemical attack, terror attack, subway accident, mine collapse, and/or a biological agent attack, etc.). Section 700 is a cross section of the distribution structure 104 embedded in the fire rated material 702.

Figure 7B:
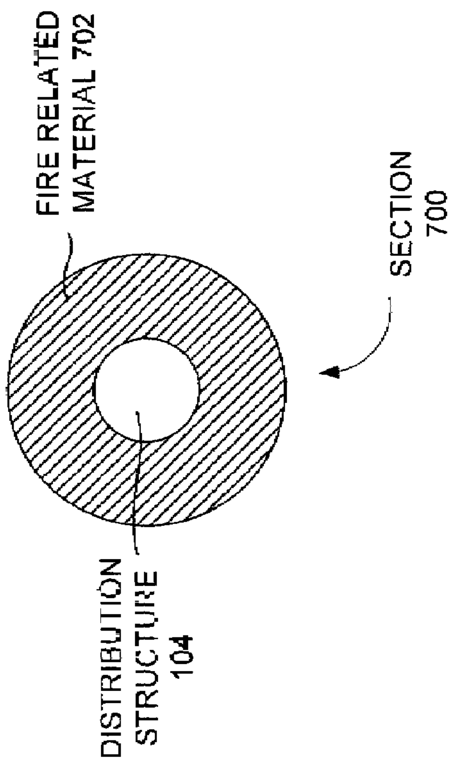
FIG. 7B is a cross sectional view of a pipe of a distribution structure embedded in a fire rated material, according to one embodiment.

FIG. 7B is a cross sectional view 700 of a piping structure embedded in a fire rated material, according to one embodiment.

Section 700 is a cross section of the distribution structure 104 embedded in the fire rated material 702.

Figure 8:
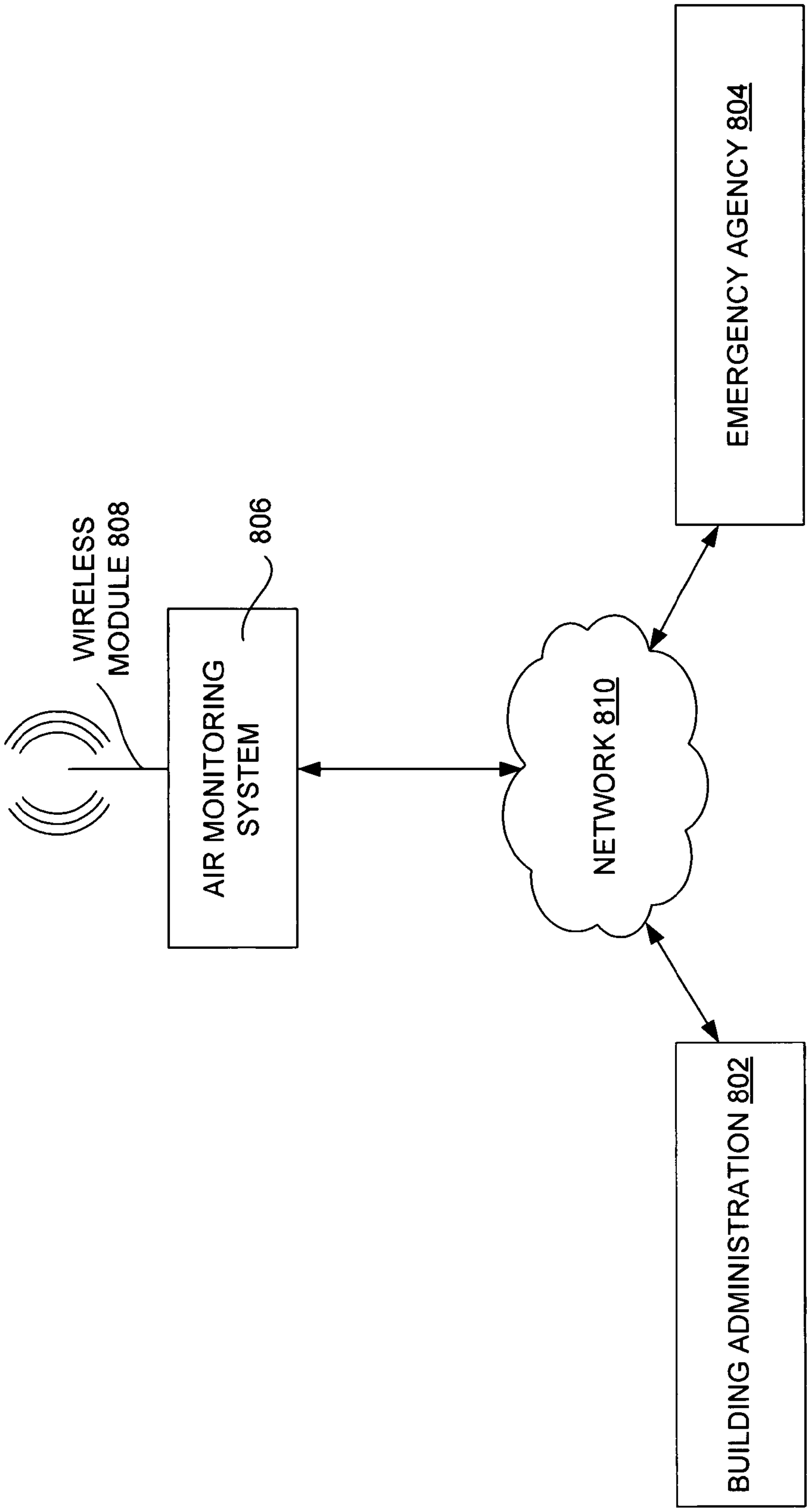
FIG. 8 is a network view of a air monitoring system that communicates building administration and an authority agency, according to one embodiment.

FIG. 8 is a network view of a air monitoring system 806 with a wireless module 808 that communicates with an building administration 802 and an authority agency 804 through a network 810, according to one embodiment.

The air monitoring system 806 may include various sensors (e.g., CO/moisture sensor 106 of FIG. 1, pressure sensor 108 of FIG. 1, and/or hazardous substance sensor, etc.) and/or status indicators regarding system readiness information (e.g., system pressure, in use, not in use, operational status, fill site usage status, fill site operational status, etc.). The air monitoring system 806 may communicate sensor readings to a building administration 802 (e.g., building management, security, and/or custodial services, etc.) such that proper maintenance measures may be taken. The air monitoring system 806 may also send alerting signals as a reminder for regular system inspection and maintenance to the building administration 802 through the network 810. The air monitoring system 806 may also communicate sensor readings to an authority agency 804 (e.g., a police station, a fire station, and/or a hospital, etc.).

Figure 9:
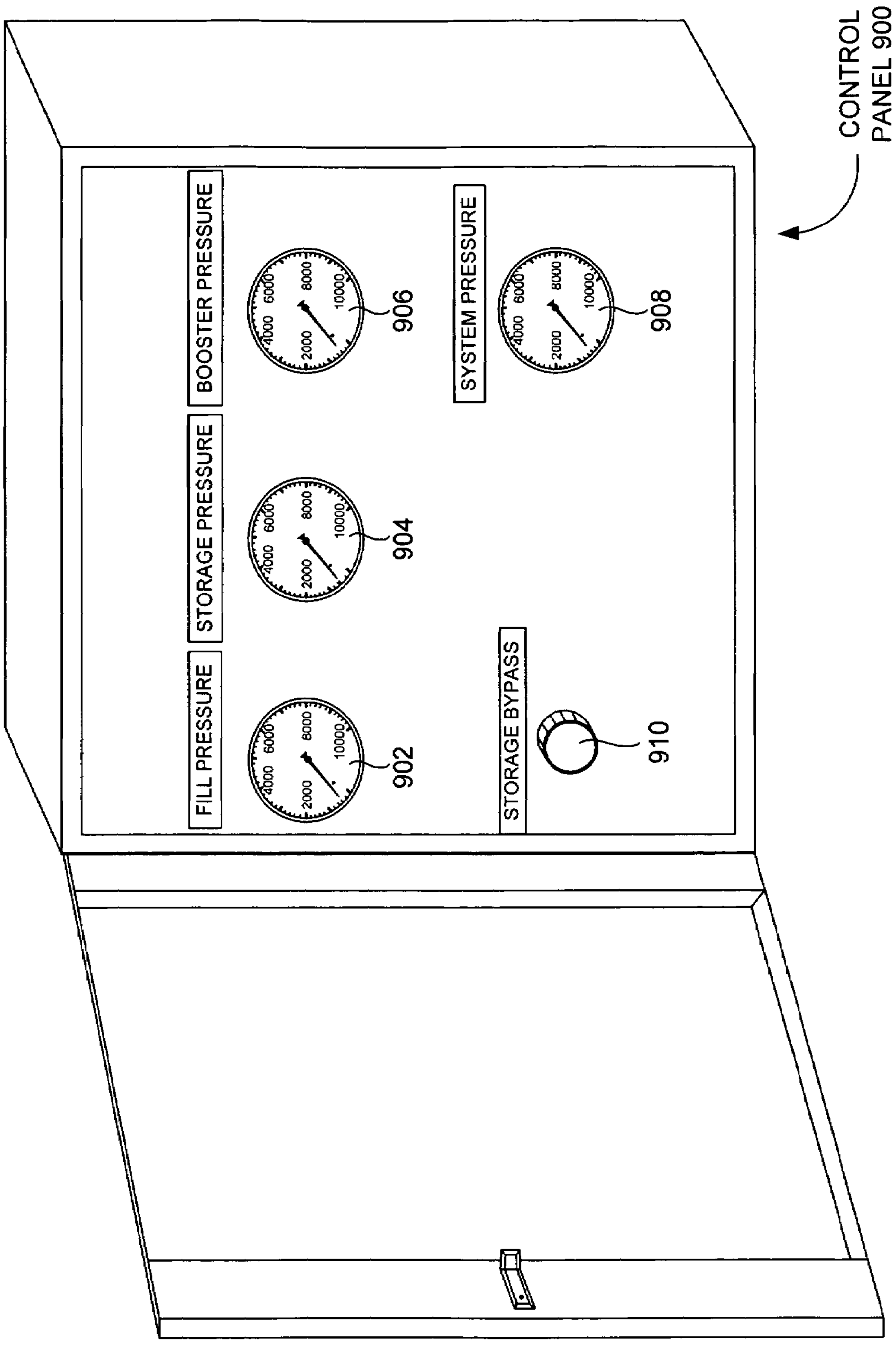
FIG. 9 is a front view of a control panel of a storage sub-system, according to one embodiment.

FIG. 9 is a front view of a control panel 900 of a air storage sub-system, according to one embodiment.

The control panel 900 includes a fill pressure indicator 902, a storage pressure indicator 904, a booster pressure indicator 906, a system pressure indicator 908 and/or a storage bypass 910. The fill pressure indicator 902 may indicate the pressure level at which breathable air is being delivered by the source of compressed air to the air distribution system (e.g., an air distribution system 150, 250, and/or 350 of FIGS. 1-3). The storage pressure indicator 904 may display the pressure level of air storage tanks in the air storage sub-system. The booster pressure indicator may display the pressure level of a booster cylinder. The system pressure indicator 908 may indicate the current pressure level of the breathable air in the air distribution system. Air may be directly supplied to the air distribution system (e.g., an air distribution system 150, 250, and/or 350 of FIGS. 1-3) through the storage bypass 910.

Figure 10:
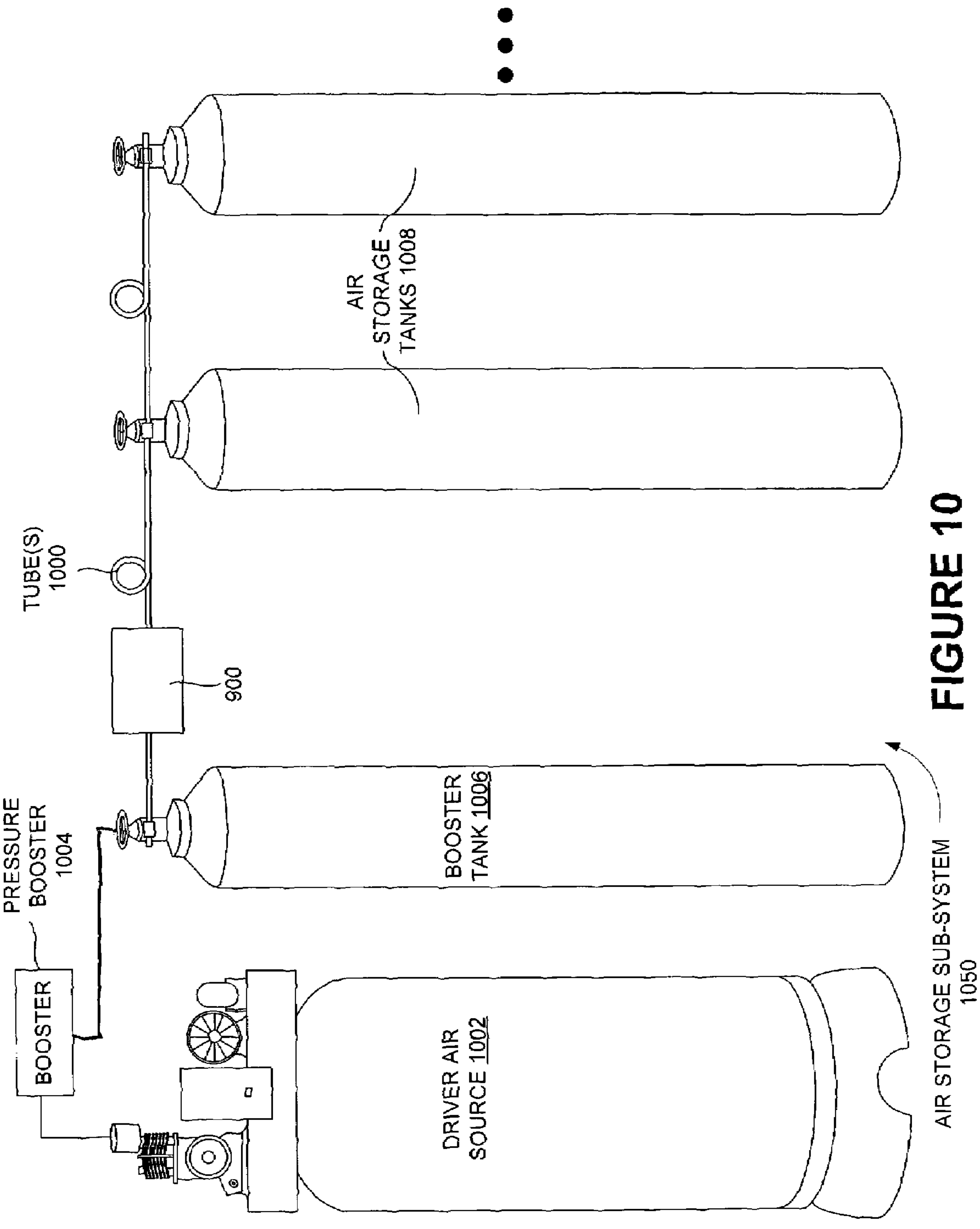
FIG. 10 is an illustration of a storage sub-system, according to one embodiment.

FIG. 10 is an illustration of a air storage sub-system 1050, according to one embodiment.

The air storage sub-system 1050 may include a control panel 900, tubes 1000, a driver air source 1002, a pressure booster 1004, a booster tank 1006, and/or any number of air storage tanks 1008. The control panel 900 may provide status information regarding the various components of the air storage sub-system 1050. The tubes 1000 may couple each of the air storage tanks 1008 to one another in a looped configuration to increase robustness of the tubes 1000. The driver air source 1002 may be used to pneumatically drive the pressure booster 1004 to maintain a higher pressure of the air distribution system such that a breathable air apparatus is reliably filled. The booster tank 1006 may store air at a higher pressure than the air stored in the air storage tanks 1008 to ensure that the air distribution system can be supplied with air that is sufficiently pressurized to fill a breathable air apparatus.

In one embodiment, the air storage sub-system 1050 may include an air storage tanks 1008 to provide a storage of air that is dispersible to multiple locations of the building structure. The number of air storage tanks 1008 of the air storage sub-system 1050 may be coupled to each other through tubes 1000 having a looped configuration to increase robustness of the tubes 1000 through preventing breakage due to stress. In addition, a booster tank (e.g., the booster tank 1006) of the air storage sub-system 1050 may be coupled to the plurality of air storage tanks to store compressed air of a higher pressure than the compressed air that is stored in the air storage tanks 1008. A driver air source 1002 of the air storage sub-system 1050 may be coupled to a pressure booster (e.g., the pressure booster 1004) to pneumatically drive a piston of the pressure booster (e.g., the pressure booster 1004) to maintain a higher pressure of the air distribution system such that a breathable air apparatus is reliably filled.

Further, the driver air source may enable the breathable air to be optimally supplied to the building structure through allowing the breathable air to be isolated from driving the pressure booster 1004. The air storage sub-system 1050 may also include an air monitoring system (e.g., the carbon monoxide sensor and moisture sensor 106 of FIGS. 1-3) to automatically track and record any of impurities and contaminants in the breathable air of the air distribution system. The air monitoring system 110 of FIGS. 1-3 may include an automatic shut down feature to suspend air dissemination to the fill stations (e.g., the fill station) in a case that any of impurity levels and contaminant levels exceed a safety threshold. The air storage sub-system 1050 may also include a pressure monitoring system (e.g., a pressure sensor 108 of FIG. 1) to continuously track and record the system pressure of the air distribution system (e.g., the air distribution system 150, 250, 350 of FIGS. 1-3). In addition, a pressure switch may be electrically coupled to an alarm system such that the alarm system is set off when the system pressure of the air distribution system (e.g., the air distribution system 150, 250, 350 of FIGS. 1-3) is outside a safety range. The pressure switch (e.g., a pressure sensor 108 of FIG. 1) may electrically transmit a warning signal to an emergency supervising station when the system pressure of the air distribution system (e.g., the air distribution system 150, 250, 350 of FIGS. 1-3) is below the prescribed level.

The air storage sub-system 1050 may include at least one indicator unit to provide status information of the air distribution system (e.g., the air distribution system 150, 250, 350 of FIGS. 1-3) including storage pressure, booster pressure, pressure of the compressed air source, and the system pressure. Further, the air storage sub-system 1050 may also include a selector valve that is accessible by an emergency personnel to isolate the source of compressed air from the air storage sub-system such that the breathable air of the source of compressed air is directly deliverable to the fill site (e.g., the fill site 102A of FIG. 6) through the distribution structure. The air storage sub-system 1050 may be housed in a fire rated enclosure that is certified to be rupture containable to withstand elevated temperatures for a period of time.

Figure 11:
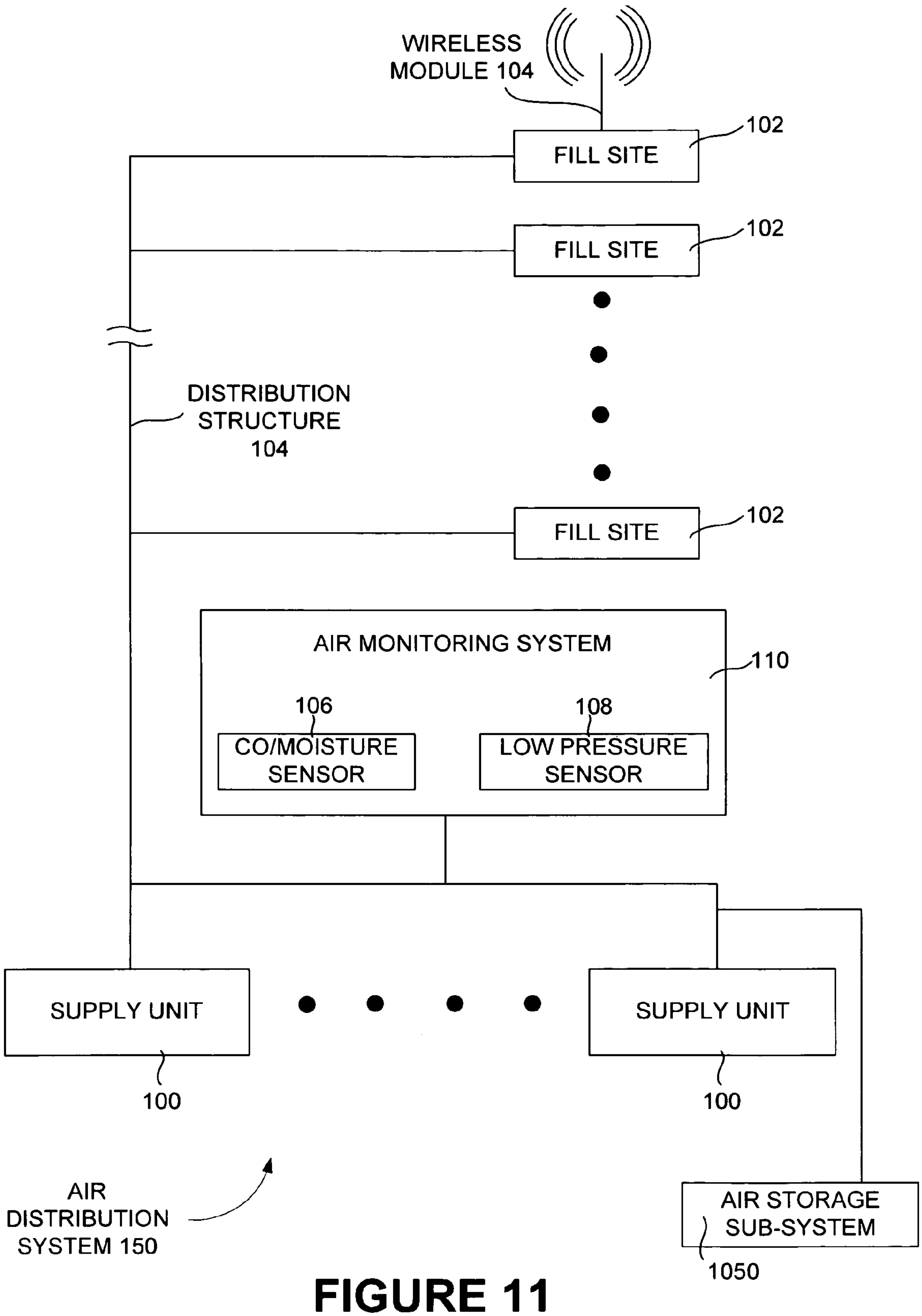
FIG. 11 is a diagram of an air distribution system having a storage sub-system, according to one embodiment.

FIG. 11 is a diagram of an air distribution system having a air storage sub-system 1050, according to one embodiment.

The air distribution system 150 may include any number of supply unit 100, any number of fill sites (e.g., the fill site 102A of FIG. 6) that are coupled to the rest of the air distribution system 150 through a distribution structure 104. The air distribution system 150 may also include a air monitoring system 110 having a CO/Moisture sensor 106 and a pressure sensor 108, and/or the air storage sub-system 1050. The air storage sub-system 1050 is as previously described. Air storage tanks 1008 and/or a booster tank 1006 of the air storage sub-system 1050 of FIG. 10 may be supplied with breathable air through a source of compressed air that is coupled to the air distribution system through the supply unit 100 and/or supplied independently of the supply unit 100. The air storage sub-system 1050 may provide a spare source of breathable air to the air distribution system (e.g., the air distribution system 150, 250, 350 of FIGS. 1-3) in addition to an external source of compressed air.

Figure 12:
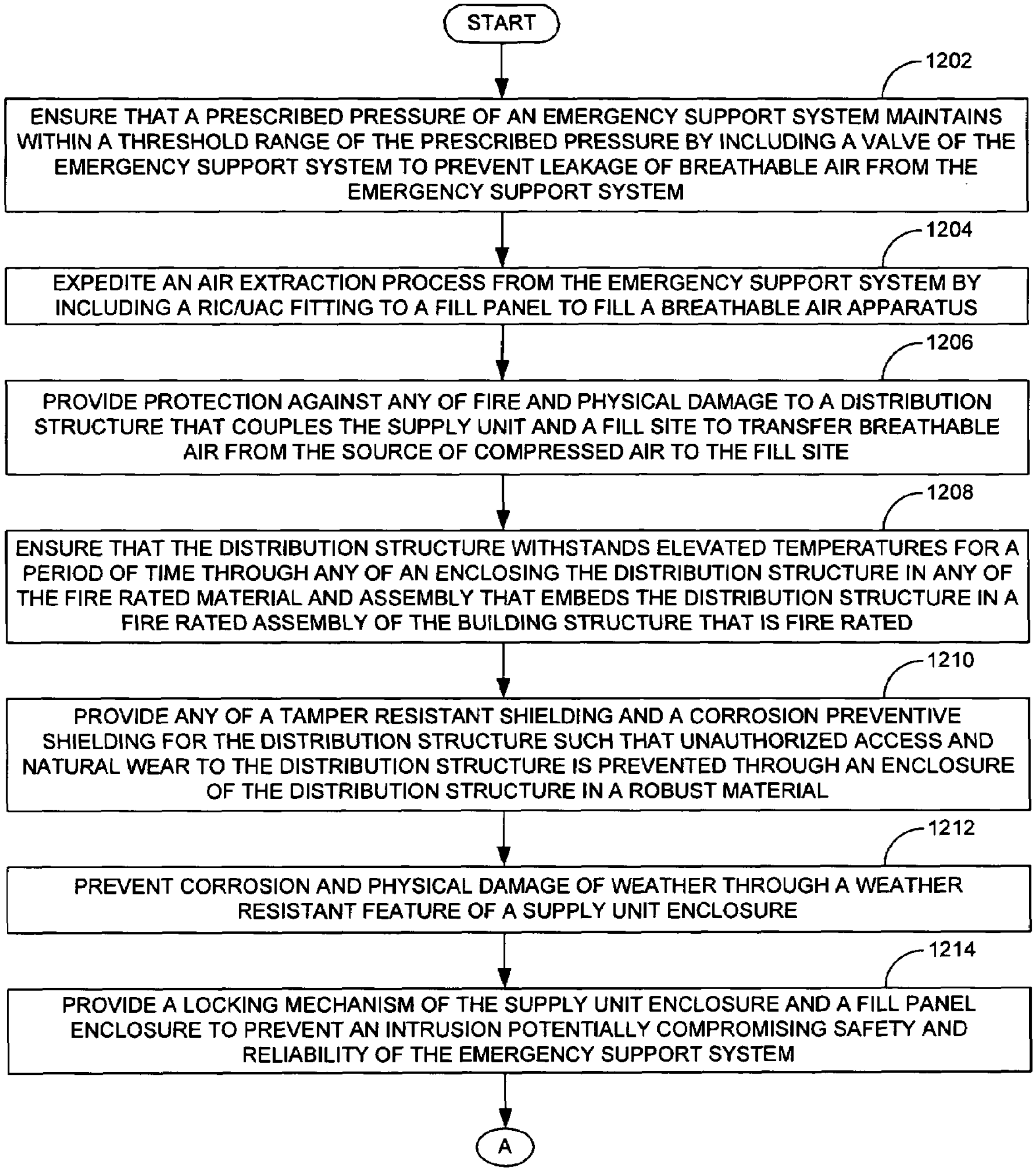
FIG. 12 is a process flow of a safety of a building structure, according to one embodiment.

FIG. 12 is a process flow of a safety of a building structure, according to one embodiment. In operation 1202, a prescribed pressure of an emergency support system (e.g., the air distribution system 150,250, 350 of FIGS. 1-3) maintains within a threshold range of the prescribed pressure may be ensured by including a valve (e.g., a valve of a series of valves 410 of FIG. 4) of the emergency support system (e.g., the air distribution system 150,250, 350 of FIGS. 1-3) to prevent leakage of breathable air from the emergency support system (e.g., the air distribution system 150,250, 350 of FIGS. 1-3). In operation 1204, an air extraction process may be expedited from the emergency support system (e.g., the air distribution system 150, 250, 350 of FIGS. 1-3) by including a RIC (rapid interventions company/crew)/UAC (universal air connection)fitting (e.g., the RIC (rapid interventions company/crew)/UAC (universal air connection connector 610 of FIG. 6) to a fill panel to fill a breathable air apparatus.

In operation 1206, protection against any of fire and physical damage to a distribution structure that couples the supply unit (e.g., a supply unit 100 of FIGS. 1-3) and a fill site to transfer breathable air from the source of compressed air to the fill site may be provided. In operation 1208, the distribution structure withstands elevated temperatures for a period of time may be ensured through any of an enclosing the distribution structure in any of the fire rated material and assembly that embeds the distribution structure in a fire rated assembly of the building structure that is fire rated.

In operation 1210, any of a tamper resistant shielding and a corrosion preventive shielding for the distribution structure may be provided such that unauthorized access and natural wear to the distribution structure is prevented through an enclosure of the distribution structure in a robust material. In operation 1212, corrosion and physical damage of weather may be prevented through a weather resistant feature of a supply unit enclosure (e.g., the supply unit enclosure 500 of FIG. 5). In operation 1214, a locking mechanism (e.g., the locking mechanism 502 of FIG. 5) of the supply unit enclosure (e.g., the supply unit enclosure 500 of FIG. 5) and a fill panel enclosure may be provided to prevent an intrusion potentially compromising safety and reliability of the emergency support system (e.g., the air distribution system 150, 250, 350 of FIGS. 1-3).

Figure 13:
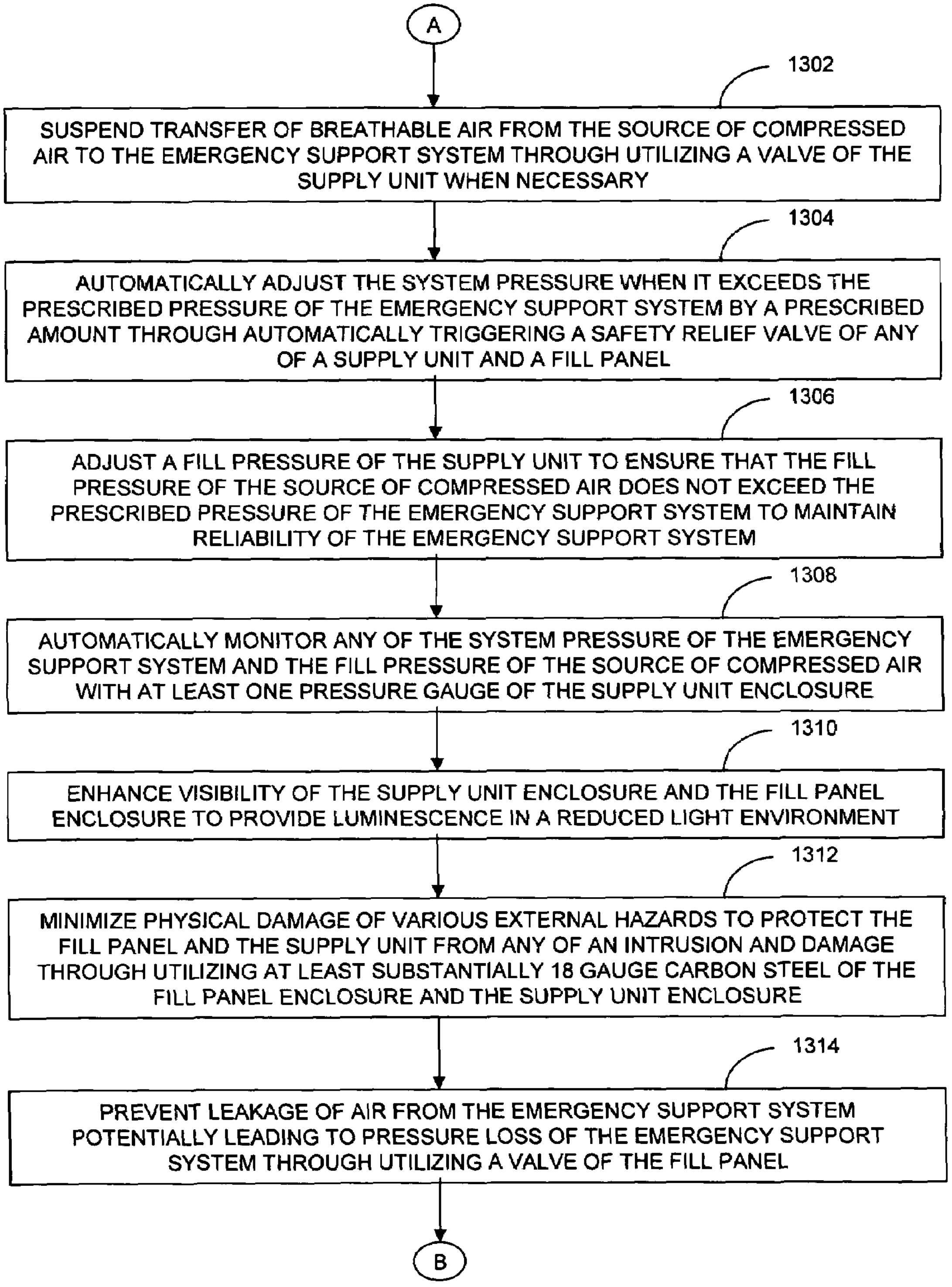
FIG. 13 is a process flow that describes further the operations of FIG. 12, according to one embodiment.

FIG. 13 is a process diagram that describes further the operations of FIG. 12, according to one embodiment. In operation 1302, transfer of breathable air from the source of compressed air to the emergency support system (e.g., the air distribution system 150, 250, 350 of FIGS. 1-3) may be suspended through utilizing a valve (e.g., a valve of a series of valves 410 of FIG. 4) of the supply unit (e.g., a supply unit 100 of FIGS. 1-3) when necessary. In operation 1304, the system pressure when it exceeds the prescribed pressure of the emergency support system (e.g., the air distribution system 150, 250, 350 of FIGS. 1-3) by a prescribed amount may be automatically adjusted through automatically triggering a safety relief valve (e.g., a valve of a series of valves 410 of FIG. 4) of any of a supply unit (e.g., a supply unit 100 of FIGS. 1-3) and a fill panel. In operation 1306, a fill pressure of the supply unit (e.g., a supply unit 100 of FIGS. 1-3) may be adjusted to ensure that the fill pressure of the source of compressed air does not exceed the prescribed pressure of the emergency support system (e.g., the air distribution system 150, 250, 350 of FIGS. 1-3) to maintain reliability of the emergency support system (e.g., the air distribution system 150, 250, 350 of FIGS. 1-3).

In operation 1308, the system pressure of the emergency support system (e.g., the air distribution system 150, 250, 350 of FIGS. 1-3) and the fill pressure of the source of compressed air may be automatically monitored with at least one pressure gauge of the supply unit enclosure (e.g., the supply unit enclosure 500 of FIG. 5). In operation 1310, visibility of the supply unit enclosure (e.g., the supply unit enclosure 500 of FIG. 5) and the fill panel enclosure may be enhanced to provide luminescence in a reduced light environment. In operation 1312, physical damage of various external hazards may be minimized to protect the fill panel and the supply unit (e.g., a supply unit 100 of FIGS. 1-3) from any of an intrusion and damage through utilizing at least substantially 18 gauge carbon steel of the fill panel enclosure and the supply unit enclosure (e.g., the supply unit enclosure 500 of FIG. 5). In operation 1314, leakage of air from the emergency support system (e.g., the air distribution system 150, 250, 350 of FIGS. 1-3) potentially leading to pressure loss of the emergency support system (e.g., the air distribution system 150, 250, 350 of FIGS. 1-3) may be prevented through utilizing a valve (e.g., a valve of a series of valves 410 of FIG. 4) of the fill panel.

Figure 14:
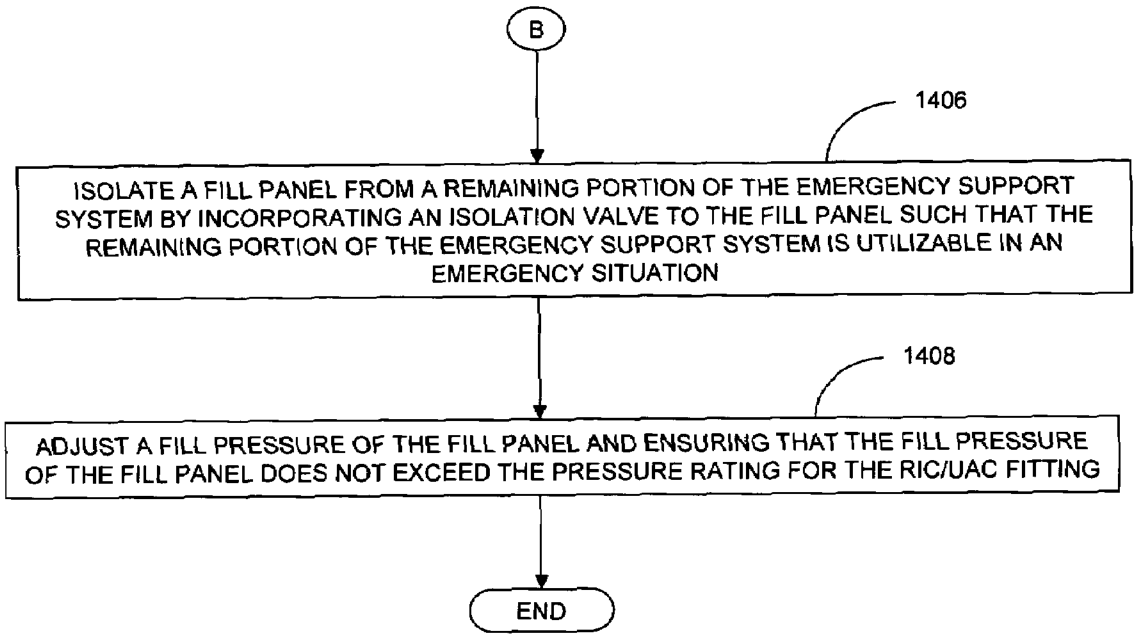
FIG. 14 is a process flow that describes further the operations of FIG. 13, according to one embodiment.

FIG. 14 is a process diagram that describes further the operations of FIG. 13, according to one embodiment. In operation 1402, a fill panel from a remaining portion of the emergency support system (e.g., the air distribution system 150, 250,350 of FIGS. 1-3) may be isolated by incorporating an isolation valve (e.g., a valve of a series of valves 410 of FIG. 4) to the fill panel such that the remaining portion of the emergency support system (e.g., the air distribution system 150, 250, 350 of FIGS. 1-3) is utilizable in an emergency situation. In operation 1404, a fill pressure of the fill panel may be adjusted and ensuring that the fill pressure of the fill panel does not exceed the pressure rating for the RIC (rapid interventions company/crew)/UAC (universal air connection) fitting (e.g., RIC (rapid interventions company/crew)/UAC (universal air connection) connector 610 of FIG. 6).

Although the present embodiments have been described with reference to specific example embodiments, it will be evident that various modifications and changes may be made to these embodiments without departing from the broader spirit and scope of the various embodiments. For example, the various devices, modules, analyzers, generators, etc. described herein may be enabled and operated using hardware circuitry (e.g., CMOS based logic circuitry), firmware, software and/or any combination of hardware, firmware, and/or software (e.g., embodied in a machine readable medium). For example, the various electrical structure and methods may be embodied using transistors, logic gates, and electrical circuits (e.g., application specific integrated ASIC circuitry).

In addition, it will be appreciated that the various operations, processes, and methods disclosed herein may be embodied in a machine-readable medium and/or a machine accessible medium compatible with a data processing system (e.g., a computer system), and may be performed in any order. Accordingly, the specification and drawings are to be regarded in an illustrative rather than a restrictive sense.

What is claimed are:

1. A method of safety of a structure, comprising:

ensuring that a prescribed pressure of an emergency support system maintains within a threshold range of the prescribed pressure by including a valve of the emergency support system to prevent leakage of breathable air from the emergency support system; wherein the prescribed pressure of the emergency support system is designated based on a municipality code that specifies a pressure rating of the breathable air apparatus that is used in an authority agency of a particular geographic location; and expediting an air extraction process from the emergency support system by including a RIC (rapid interventions company/crew)/UAC (universal air connection) fitting to a fill panel to fill a breathable air apparatus.

2. The method of claim 1 further comprising providing protection against any of fire and physical damage to a distribution structure that couples the supply unit and a fill site to transfer breathable air from the source of compressed air to the fill site.

3. The method of claim 2 further comprising ensuring that the distribution structure withstands elevated temperatures for a period of time through any of an enclosing the distribution structure in any of the fire rated material and assembly that embeds the distribution structure in a fire rated assembly of the building structure that is fire rated.

4. The method of claim 3 further comprising automatically adjusting the system pressure when it exceeds the prescribed pressure of the emergency support system by a prescribed amount through automatically triggering a safety relief valve of any of a supply unit and a fill panel.

5. The method of claim 3 further comprising automatically monitoring any of the system pressure of the emergency support system and the fill pressure of the source of compressed air with at least one pressure gauge of the supply unit enclosure.

6. The method of claim 3 further comprising enhancing visibility of the supply unit enclosure and the fill panel enclosure to provide luminescence in a reduced light environment.

7. The method of claim 2 further comprising providing any of a tamper resistant shielding and a corrosion preventive shielding for the distribution structure such that unauthorized access and natural wear to the distribution structure is prevented through an enclosure of the distribution structure in a robust material.

8. The method of claim 7 further comprising adjusting a fill pressure of the supply unit to ensure that the fill pressure of the source of compressed air does not exceed the prescribed pressure of the emergency support system to maintain reliability of the emergency support system.

9. The method of claim 1 further comprising preventing corrosion and physical damage of weather through a weather resistant feature of a supply unit enclosure.

10. The method of claim 9 further comprising providing a locking mechanism of the supply unit enclosure and a fill panel enclosure to prevent an intrusion potentially compromising safety and reliability of the emergency support system.

11. The method of claim 10 further comprising minimizing physical damage of various external hazards to protect the fill panel and the supply unit from any of an intrusion and damage through utilizing at least substantially 18 gauge carbon steel of the fill panel enclosure and the supply unit enclosure.

12. The method of claim 11 further comprising adjusting a fill pressure of the fill panel and ensuring that the fill pressure of the fill panel does not exceed the pressure rating for the RIC (rapid interventions company/crew)/UAC (universal air connection) fitting.

13. The method of claim 1 further comprising suspending transfer of breathable air from the source of compressed air to the emergency support system through utilizing a valve of the supply unit when necessary.

14. The method of claim 1 further comprising preventing leakage of air from the emergency support system potentially leading to pressure loss of the emergency support system through utilizing a valve of the fill panel.

15. The method of claim 1 further comprising isolating a fill panel from a remaining portion of the emergency support system by incorporating an isolation valve to the fill panel such that the remaining portion of the emergency support system is utilizable in an emergency situation.

* * * * *